(12) United States Patent
Bhaskar et al.

(10) Patent No.: US 7,522,664 B1
(45) Date of Patent: Apr. 21, 2009

(54) REMOTE LIVE VIDEO INSPECTION

(76) Inventors: Krishnamurthy Bhaskar, 1061 Queensbridge Ct., San Jose, CA (US) 95120; Mark J. Roulo, 115 Chetwood Dr., Mountain View, CA (US) 94043; Michael Van Riet, 594 Calle Siena, Morgan Hill, CA (US) 95037; Stewart K. Hill, 802 Kyle St., San Jose, CA (US) 95127

( * ) Notice: Subject to any disclaimer, the term of this patent is extended or adjusted under 35 U.S.C. 154(b) by 837 days.

(21) Appl. No.: 10/659,223

(22) Filed: Sep. 10, 2003

(51) Int. Cl.
  *H04N 7/12* (2006.01)
  *H04N 7/18* (2006.01)
  *G06K 9/00* (2006.01)

(52) U.S. Cl. .................. 375/240.01; 348/126; 382/145

(58) Field of Classification Search ............ 375/240.01; 725/38; 702/188; 382/141, 144, 145, 232; 348/125
  See application file for complete search history.

(56) References Cited

U.S. PATENT DOCUMENTS

| | | | | |
|---|---|---|---|---|
| 5,845,166 A * | 12/1998 | Fellegara et al. | ............ | 396/429 |
| 5,926,208 A * | 7/1999 | Noonen et al. | ............ | 348/14.13 |
| 6,005,613 A * | 12/1999 | Endsley et al. | ............ | 348/231.6 |
| 6,370,487 B1 * | 4/2002 | Dorough | .................... | 702/188 |
| 6,512,858 B2 * | 1/2003 | Lyon et al. | .................. | 382/305 |
| 6,583,813 B1 * | 6/2003 | Enright et al. | .............. | 348/150 |
| 6,721,952 B1 * | 4/2004 | Guedalia et al. | .............. | 725/38 |
| 7,308,158 B2 * | 12/2007 | Herbert et al. | .............. | 382/298 |

* cited by examiner

*Primary Examiner*—Gims S Philippe

(57) ABSTRACT

A system for inspecting a substrate. An inspector includes a sensor that inspects the substrate and produces a video stream. A control interface sends and receives a control stream, and a network receives and transports the video stream and the control stream as two separate data streams. A desktop receives the video stream and the control stream as two separate data streams. The desktop has a display that presents the video stream, and a user interface controls that control the operation of the inspector, using the control stream across the network.

19 Claims, 1 Drawing Sheet

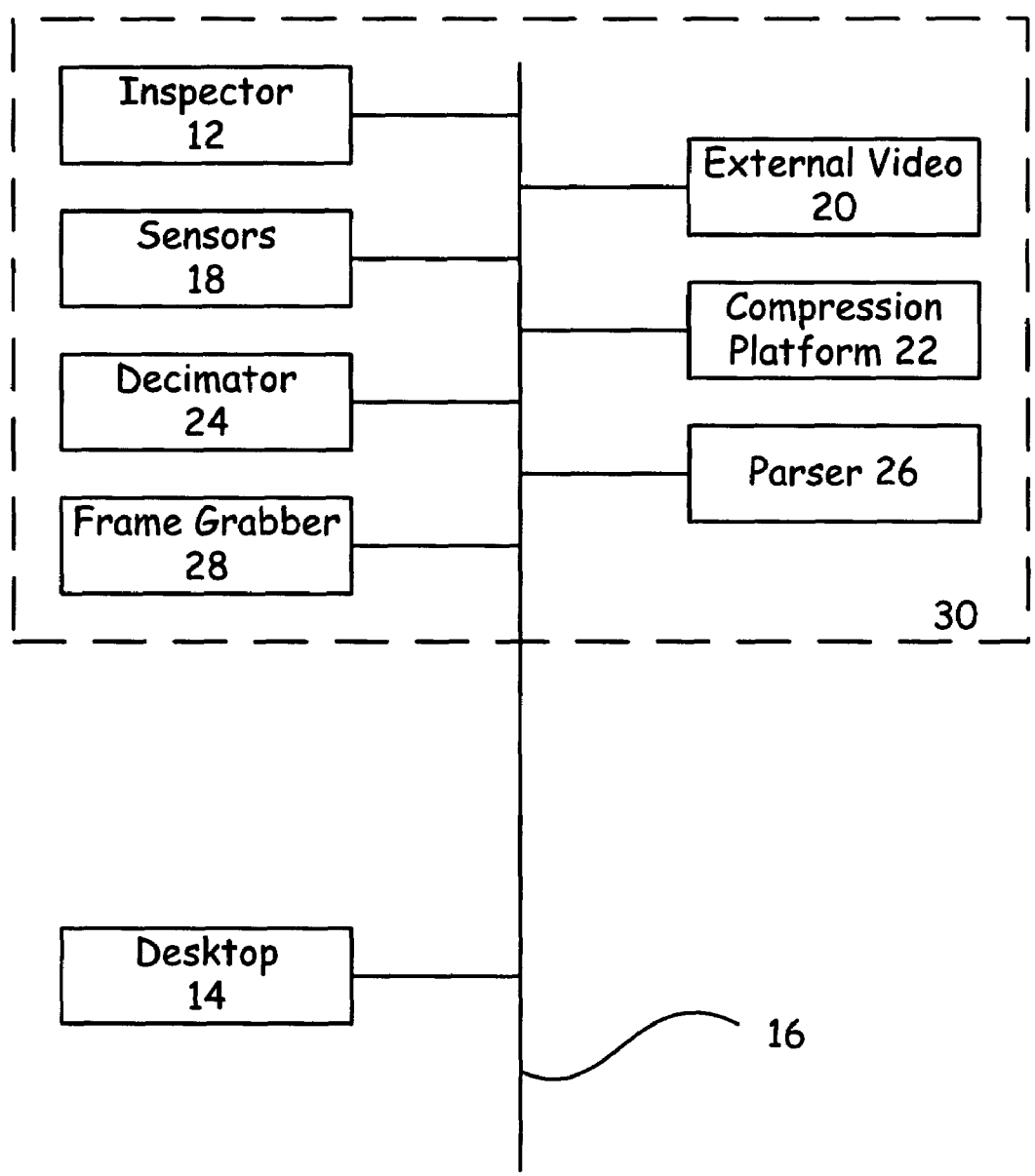

REMOTE LIVE VIDEO INSPECTION

FIELD

This invention relates to the field of instrumentation. More particularly, this invention relates to the control and operation of inspection equipment from a remote location across a network.

BACKGROUND

As the size of integrated circuits shrinks, the number of devices within an integrated circuit has risen. For example, a rule of thumb common called Moore's Law states that the number of transistors in a state of the art integrated circuit generally doubles every eighteen months. For many years this rule of thumb has generally been true. Thus, the increase in the number of cells within an integrated circuit has grown exponentially rather than linearly. Obviously, over the past several years the number of cells within a single integrated circuit has virtually exploded.

This tremendous and rapid increase in the number of active devices within an integrated circuit has come about as a result of innovation and changes in the way that the devices are designed and fabricated. Thus, many different issues have been overcome in accomplishing this increase in the capacity of integrated circuits. At the same time, however, this increase in the complexity and capacity of integrated circuits has created new challenges in regard to other aspects of integrated circuit fabrication, such as inspection.

Integrated circuits are typically inspected throughout the fabrication process, both to ensure that the processes used to fabricate the integrated circuits are in control, and also to ensure that the structures formed by the various processes have the proper characteristics, and are not malformed, scratched, or contaminated. For a variety of reasons, inspections of the substrates used in integrated circuit fabrication, such as semiconductor wafers and masks and reticles, have become much more complex than they previously were. For example, the structures being formed are much smaller than they previously were, as described above. This has resulted in the inspection systems becoming commensurately more complex, so as to be able to adequately inspect the smaller structures. For this and other reasons, inspection systems require more set up and tuning than in times past, in order to provide the desired benefits.

Unfortunately, training on such equipment typically requires that either the vendor travels to the customer site, or the customer travels to the vendor site. Additionally, set up or other maintenance of the equipment often requires the vendor to travel to the customer site, if the customer is unable to achieve the desired results on their own. Such travel is expensive and time consuming.

What is needed, therefore, is a system by which an inspection tool can be operated remotely, so that setup, inspection, and training can be accomplished remotely, without having to be physically in front of the inspection tool.

SUMMARY

The above and other needs are met by a system for inspecting a substrate. An inspector includes a sensor that inspects the substrate and produces a video stream. A control interface sends and receives a control stream, and a network receives and transports the video stream and the control stream as two separate data streams. A desktop receives the video stream and the control stream as two separate data streams. The desktop has a display that presents the video stream, and user interface controls that control the operation of the inspector, using the control stream across the network.

In this manner the present invention provides a tremendous amount of capability to a wafer, reticle, or metrology inspection system. The ability to effectively control these inspection systems remotely enables, for example, teams to develop software for, test, and train users on a single inspection system around the clock without locating and maintaining multiple systems around the world. Using the tool remotely, rather than visiting the site at which it is located, reduces travel time and costs. A user can respond to issues and provide assistance in a shorter period of time if not required to gown up and enter the clean room, or even to drive to the fabrication facility from home.

In various preferred embodiments, the inspector is an optical inspection system, electron beam inspection system, optical review system, or electron beam review system. The substrate is preferably one of a semiconductor wafer with integrated circuitry at least partially formed thereon, or a mask for use in patterning integrated circuits on a semiconductor wafer. In one embodiment an additional video source selectively produces an additional video stream for receipt by the desktop, under control of the user interface controls on the desktop.

The user interface on the desktop preferably selectively sets characteristics of the video stream prior to delivery of the video stream from the sensor to the desktop. Preferably, a compressor selectively compresses the video stream prior to delivery of the video stream from the sensor to the desktop, where the compressor most preferably compresses the video stream to a variable degree as specified through the user interface controls on the desktop. A decimator preferably selectively down samples the video stream prior to delivery of the video stream from the sensor to the desktop, where the decimator most preferably down samples the video stream to a variable degree as specified through the user interface controls on the desktop. Preferably, a parser selectively crops the video stream prior to delivery of the video stream from the sensor to the desktop, where the parser most preferably crops the video stream to a variable degree as specified through the user interface controls on the desktop. A codec preferably selectively sets a frame rate of the video stream prior to delivery of the video stream from the sensor to the desktop, where the codec most preferably sets the frame rate of the video stream to a variable degree as specified through the user interface controls on the desktop.

In one embodiment, the compressor, decimator, parser, and codec all reside within the inspector.

BRIEF DESCRIPTION OF THE DRAWINGS

Further advantages of the invention are apparent by reference to the detailed description when considered in conjunction with the FIGURE, which is not to scale so as to more clearly show the details, wherein like reference numbers indicate like elements, and which depicts a functional block diagram of a remotely controlled inspection system according to a preferred embodiment of the present invention.

DETAILED DESCRIPTION

The general purpose of the preferred embodiment of the present invention is to enable the remote operation of inspection equipment over a network. With reference to the FIGURES, the inspection equipment is generally referred to herein as the inspector 12, and the station that remotely controls the inspector is generally referred to herein as the desktop 14. The desktop 14 may take one or more of a variety of different configurations, such as a dedicated controller that is specifically equipped to control the inspector 12, and which is connected to the inspector 12 by a dedicated data connection. However, in the most preferred embodiments, the desktop 14 is a general purpose desktop type computer, which is running software designed to enable the computer to connect to the inspector 12 over a general purpose computer network 16.

The inspector 12 may also take one or more of a variety of different configurations, such as instrumentation that is used for one or more of metrology, materials analysis, and defect review, such as an electron beam inspection system, electron beam review system, or optical review system. Most preferably, the inspector is an instrument that is used for inspection of substrates of different types that are used in the fabrication of integrated circuits. Thus, the substrates on which the inspector 12 operates may also be one or more of a variety of different types, such as semiconductor wafers in various stages of processing, masks, and reticles. The term "inspection" is generally used herein in reference to the function of the inspector 12. It is appreciated that, as used herein, the term "inspection" includes functions such as metrology, review, analysis, defect detection, and other such functions.

Preferred embodiments of the system 10 include both the ability to control the operation of the inspector 12 from the desktop 14, and the ability to deliver high quality live video from the inspector 12 to the desktop 14. These capabilities enable the desktop 14 to review defects and examine the substrate structures and patterns that are necessary to set up and execute control programs, generally referred to as recipes herein, on the inspector 12. The remote control of the inspector 12 may be from one or more of a number of different locations, such as from an office residing in the same building as the inspector 12, from an employee's home, or from any other location around the world.

Most preferably, the network 16 between the desktop 14 and the inspector 12 is a relatively high speed network, which enables the speedy transmission of the high quality live video feed from the inspector 12 to the desktop 14. Thus, the network 16 preferably includes means such as wired networks having data bandwidths of ten, one hundred, or one thousand megabits per second, wireless networks having data bandwidths of preferably at least about two megabits per second, and connections across a global integrated network such as the Internet, preferably having data bandwidths of at least about one quarter megabits per second. However, as described in more detail below, networks 16 having data bandwidths even much lower than these are contemplated by the present invention.

It is most preferred that the communication between the inspector 12 and the desktop 14 across the network 16 have some type of security enabled, so that an unauthorized third party cannot surreptitiously gain control of the inspector 12, or receive the video stream delivered from the inspector 12. Thus, methods such as data encryption and compression can be used to not only reduce the bandwidth required by the communication between the inspector 12 and the desktop 14, but can also be used to protect the confidentiality of the data stream. This is especially important when the desktop 14 is communicating with the inspector 12 across an open network 16 such as the Internet. In such a case, a protocol such as a Virtual Private Network is preferably used to secure the communication.

The preferred embodiment of the present invention divides the problems associated with the remote control of an instrument across a network into two pieces. The first piece is manipulating the user interface of the inspector 12 from the desktop 14. As briefly introduced above, the desktop 14 is preferably a computer running software that presents a user interface of the inspector 12 for display and control over the network 16. The user interface controls and feed back are preferably contained within a control data stream.

Many different remote desktop software packages are currently available for purchase on the general market, such as NetMeeting, NetOp, RAdmin, VNC, and PC Anywhere. Some of these packages contain a subset of the functionality described herein, and are mentioned so as to provide a point of reference in the description of the embodiments of the invention. However, remote operation of inspection equipment using only remote desktop software such as that described above is completely inadequate because of the slow speed and the low resolution of the video that such programs provide. Using such programs, video can be sent to the desktop 14 from the inspector 12, but at a very low frame rate, with poor quality, and at a large cost in network 16 bandwidth. Further, on some inspectors 12, the video signal is sent directly to a video card, and thereby completely bypassing the operating system. Under these circumstances, remote desktop software cannot capture the video feed at all. These shortcomings severely limit the ability to effectively operate the inspection equipment from a remote location using only commercially available remote desktop software.

Thus, the second piece of the system is the delivery of live video. The operation of an inspector 12 for substrates such as semiconductor wafers in various stages of processing, reticles, and metrology is typically heavily dependant on the high quality and real time video provided by sensors 18, such as a microscope and camera installed inside the inspector 12. The video feed enables an operator to inspect microscopic defects and patterns on the substrate. The remote desktop software described above, which is generally available on the market, tends to provide very low quality video that is insufficient for the present purposes, in that it is neither fast enough to enable adequate remote control of the inspector 12, nor does it provide a video stream of high enough resolution to enable the detection of small defects and other structures.

Thus, in the preferred embodiment of the present invention, video compression is used to transmit the live video from the inspector 12 to the desktop 14 in a video stream that is separate from the control stream. The video stream preferably has a relatively high refresh rate, high image quality, and relatively low bandwidth requirements. The video compression that enables these characteristics of the video stream can be either loss-less or lossy, and is performed in either a hardware-based or a software-based compression platform 22. The compression platform 22 that performs the compression can reside on the inspector 12 itself, on a separate computer or external compression hardware that captures the video output of the inspector 12, or on a dedicated hardware card installed on either the inspector 12 or a separate computer.

However, because video compression is a computationally intensive operation, the video stream is most preferably compressed using dedicated hardware, which dedicated hardware tends to operate faster than software compression, and thus enables a higher refresh rate and a higher image resolution. Dedicated hardware also does not use system processor resources on the inspector 12, which may already be taxed by their primary application.

The selection of one of lossy or loss-less compression is not so clear cut. On the one hand, a completely loss-less compression algorithm tends to produce the highest quality video stream, as every single pixel of information captured by the sensors 18 at the inspector is reproduced exactly on the desktop 14. However, such loss-less compression tends to require more bandwidth on the network 16 than a lossy compression, which degrades the image quality to varying degrees based upon the selected lossy compression algorithm. In some applications that have a high enough available bandwidth over the network 16, loss-less compression is preferred, because there is ample bandwidth to deliver the amount of data in the video stream, and a higher quality picture is delivered. However, in other application, such as when the video stream is delivered over a slower network 16, lossy compression is desired. Even though the quality of the images that are delivered is reduced, the lossy compression enables the video stream to be delivered from the inspector 12 to the desktop 14 at a usable rate.

Most preferably, the desktop 14 includes a control, such as through the control stream between the desktop 14 and the inspector 12, which provides the user with the option to select either lossy or loss-less compression, and most preferably enables the selection of the degree of loss when a lossy compression is selected. Certain compression standards, such as video JPEG, already provide such selection of the degree of loss in the compression. The compression can be accomplished on every video frame independently, or by compressing the differences between one frame and the next. Algorithms for video compression also include QVIX, MJPEG2000, various MPEG compression schemes, and wavelet methods.

The video stream from the inspector 12 can also contain the video feed from one or more additional sources 20. For example, the video stream predominantly comprises the video feed from the sensors 18 that are inspecting the substrates. However, the video stream can alternately or additionally include a video stream from a camera 20 that monitors the operation of the same or related equipment, such as a robotic substrate handler that loads and unloads the substrates from the inspector 12.

The preferred embodiments of the present invention include a crop and zoom capability. Many video sources provide images that are 640 pixels by 480 pixels, which is generally referred to as VGA resolution. Even using the best compression available today, the bandwidth requirements for a video stream of this size are well beyond the capability of standbard home broadband Internet connections and most dedicated overseas network lines. These types of connections are only capable of transferring smaller video sizes, for example, 320 pixels by 240 pixels (quarter VGA) or even 160 pixels by 120 pixels.

Simply shrinking the full-size video feed by down sampling it to a size that works over limited bandwidth networks tends to reduce the resolution and amount of detail in the image that is delivered to the desktop 14. This is unacceptable for many inspector 12 applications, because the defects and features on inspected wafers and reticles are so small. As mentioned above, any loss of resolution in this manner tends to render the user less effective at finding defects and determining proper inspection settings. The crop and zoom feature of the present invention preferably enables the user to choose between a down sampled video stream, a video stream that includes a cropped section of the full size image at the original resolution, or a combination of down sampling and cropping. This capability is preferably user selectable from the desktop 14, and is not unchangeably set at the inspector 12. However, the appropriate video stream is preferably configured at the inspector 12 before delivery across the network 16, so as to reduce the bandwidth across the network 16 as desired.

For example, the full-size video image from the inspector 12 might be of VGA resolution. However, this video size may be too large to compress and transmit over the selected network 16. The crop and zoom feature enables the user to receive a smaller video stream, with a choice of reducing either the field of view or the resolution. By reducing the resolution to quarter VGA using a decimator 24, for example, the video stream requires considerably less bandwidth and covers the same field of view as the VGA video stream. However, it lacks the resolution and detail of the VGA video stream.

Another method of reducing the bandwidth required on the network 16 is to send just a portion of the VGA video stream, which portion covers an area of interest within the full VGA frame. Thus, a 320 by 240 pixel image can be sent, for example, but rather than sampling the entire VGA frame down to this number of pixels, as is done with the quarter VGA resolution, a frame of 320 by 240 pixels is cut out from the larger 640 by 480 VGA frame, such as by using a parser 26, and delivered as the video stream. Thus, this cropped and zoomed frame includes the same number of pixels as the lower resolution quarter VGA frame, but only depicts a portion of the full frame at the full resolution of the original VGA frame. Thus, the detail and resolution is the same as the original image, but the field of view is reduced. Most preferably, the user is able to remotely move the location of this cropped view within the full video frame, in order to search for detail that might be present anywhere within the full view.

Though the desktop 14 in this embodiment does not display the full video frame that is available on the inspector 12, the user can preferably switch between the video stream modes that preserve either field of view or resolution, depending on the need at the time. In even more limited bandwidth situations, smaller video images can be transmitted with even more combinations of down sampling and cropping than are described above.

In a most preferred embodiment, the degree of down sampling and cropping are continuously variable, such as with a slider on the user interface displayed at the desktop 14. For example, at a given point in time, such as when the remote access between the desktop 14 and the inspector 12 is established, or at other times as desired, a routine could be executed that determines the reliable speed of the network 16. This speed is then used to determine a maximum video stream delivery bandwidth. The user at the desktop 14 then uses a slide control on the user interface displayed at the desktop 14 to variably allocate the maximum video stream delivery bandwidth between resolution and frame size. At one end of the control, all of the video stream delivery bandwidth is used by the full resolution of the originating video stream, with a relatively small frame size. At the other end of the control, all of the video stream delivery bandwidth is used by the full frame size of the originating video stream, with a relatively small resolution.

Thus, to the user at the desktop 14, the control appears to only zoom in and out on a desired portion of the video stream that is displayed on the desktop 14, while the control software within the control stream takes care of automatically adjusting the frame size and the down sampling of the delivered video stream as required so as to not exceed the maximum video stream delivery bandwidth. Thus, by zooming in on a specific portion of the image delivered to the desktop 14, the user would actually be increasing the resolution of that portion of the image that is displayed, rather than decreasing the resolution of the image portion, as typically occurs when zooming an image. Of course, if the maximum video stream delivery bandwidth is sufficiently great, then all frames can be delivered at full resolution.

In one embodiment the user can also control at the desktop 14 the refresh rate of the video images, or in other words can control the number of video frames that are delivered per unit length of time, such as with a codec 28. In alternate embodiments, however, the refresh rate is specified at a default value by the interface software running on the desktop 14.

Preferably, the desktop 14 has complete control over all of the various characteristics of the video stream that is delivered, including the degree of down sampling, the degree of crop and zoom, selection of a color video stream or a grayscale video stream, and selection of the desired video source. Thus, the desktop 14 operator receiving the video stream has complete control over what is displayed. Traditionally, such control is specified at the server side of a remote connection, such as at the inspector 12, and is not adjustable remotely, such as at the desktop 14.

In one embodiment, all of the functions of the compressor 22, decimator 24, parser 26, and codec 28 reside locally within a unified inspector system 30. In other embodiments, the functions of the compressor 22, decimator 24, parser 26, and codec 28 reside on hardware platforms that are external to the inspector 12. However, as mentioned above, preferably all such functions can be controlled through the control stream using the user interface presented on the desktop 14.

The ability to remotely control the inspector 12 from the desktop 14, and simultaneously view real time high quality video, provides capability that has been heretofore unrealized. Software for the inspector 12 can be developed and tested remotely without the benefit of having an inspector 12 on-site. Users from around the world can receive training on the latest systems, without traveling to the factory site where the inspector 12 is being developed. These users can also control local inspectors 12 from their desk or their home, reducing the need to enter the clean room or even the fabrication site. Expert users can adjust the settings of inspectors 12 located anywhere in the world where there is network access, thereby extending their expertise instantaneously without travel and its associated costs and delays.

In one simplified embodiment of the invention, a STEALTH 2351 inspection System, available from KLA-Tencor Technologies of San Jose Calif., is used as the inspector 12. The STEALTH uses a personal computer hardware platform as a controller, on which the Microsoft Windows operating system is loaded as the environment for the user interface. A software package such as NetOp remote desktop software can thus be installed on the inspector 12. This allows the graphical user interface of the STEALTH to be controlled remotely over a network 16, and provides the user interface control portion of the system 10.

The STEALTH produces a component video signal as an output, which presents the microscope 18 feed from the inspector 12, overlaid with graphics. This component video signal is fed into an encoder box which converts the signal to an S-Video signal, which is in turn delivered to a video capture card on a separate computer sitting next to the inspection tool. SightSpeed video conferencing software is used to compress the video signal and transmit it over the network 16. The remote desktop computer 14 also uses NetOp to display and control the graphical user interface of the inspector 12. The desktop 14 also uses SightSpeed to display the live video stream from the microscope 18 of the inspector 12. A user sitting at the desktop 14 thereby has the capability of running the inspector 12 in a manner that is almost as effective as sitting in front of the tool.

In one embodiment, the software application that runs the inspector 12 is written in such a way as to enable the user interface portion of the application to be executed on the desktop 14, where the user interface portion communicates across the network with a machine control portion of the application that runs on the inspector 12. In this embodiment, the video generated by the inspector 12 is preferably embedded directly into the user interface presented on the display of the desktop 14, simulating even more closely the experience of sitting directly in front of the inspector 12. Thus, in this embodiment the control stream is not separate from the video stream as described above. Instead, there is a single integrated stream of data between the desktop 14 and the inspector 12. In this embodiment, the desktop 14 actually is the user interface of the inspector 12.

The foregoing description of preferred embodiments for this invention has been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A system for inspecting a substrate, the system comprising:
    an inspector having a sensor that inspects the substrate and produces a video stream, and a control interface adapted to send and receive a control stream,
    a network adapted to receive and transport the video stream and the control stream as two separate data streams,
    a desktop for receiving the video stream and the control stream as two separate data streams, the desktop having a display adapted to present the video stream, and the desktop having user interface controls adapted to control operation of the inspector by use of the control stream across the network, and
    a parser adapted to selectively crop the video stream prior to delivery of the video stream from the sensor to the desktop, where the selective cropping produces a cropped view and reduces a size of the video stream, and a location of the cropped view within a full video frame of the video stream is remotely selectable from the desktop via the control interface.

2. The system of claim 1, wherein the inspector is one of an optical inspection system, electron beam inspection system, electron beam review system, and optical review system.

3. The system of claim 1, wherein the substrate is a semiconductor wafer with integrated circuitry at least partially formed thereon.

4. The system of claim 1, wherein the substrate is a mask for use in patterning integrated circuits on a semiconductor wafer.

5. The system of claim 1, further comprising an additional video source adapted to selectively produce an additional video stream for receipt by the desktop, under control of the user interface controls on the desktop.

6. The system of claim 1, wherein the user interface on the desktop selectively sets characteristics of the video stream prior to delivery of the video stream from the sensor to the desktop.

7. The system of claim 1, further comprising a compressor adapted to selectively compress the video stream prior to delivery of the video stream from the sensor to the desktop.

8. The system of claim 1, further comprising a compressor adapted to selectively compress the video stream prior to delivery of the video stream from the sensor to the desktop, where the compressor compresses the video stream to a variable degree as specified through the user interface controls on the desktop.

9. The system of claim 1, further comprising a decimator adapted to selectively down sample the video stream prior to delivery of the video stream from the sensor to the desktop.

10. The system of claim 1, further comprising a decimator adapted to selectively down sample the video stream prior to delivery of the video stream from the sensor to the desktop, where the decimator down samples the video stream to a variable degree as specified through the user interface controls on the desktop.

11. The system of claim 1, wherein the parser crops the video stream to a variable degree as specified through the user interface controls on the desktop.

12. The system of claim 1, further comprising a codec adapted to selectively set a frame rate of the video stream prior to delivery of the video stream from the sensor to the desktop.

13. The system of claim 1, further comprising a codec adapted to selectively set a frame rate of the video stream prior to delivery of the video stream from the sensor to the desktop, where the codec sets the frame rate of the video stream to a variable degree as specified through the user interface controls on the desktop.

14. A system for inspecting a substrate, the system comprising:
an inspector having a sensor that inspects the substrate and produces a video stream, and a control interface adapted to send and receive a control stream,
a network adapted to receive and transport the video stream and the control stream,
a desktop for receiving the video stream and the control stream, the desktop having a display adapted to present the video stream, and the desktop having user interface controls adapted to control operation of the inspector by use of the control stream across the network,
a compressor adapted to selectively compress the video stream prior to delivery of the video stream from the sensor to the desktop,
a decimator adapted to selectively down sample the video stream prior to delivery of the video stream from the sensor to the desktop,
a parser adapted to selectively crop the video stream prior to delivery of the video stream from the sensor to the desktop, where the selective cropping produces a cropped view and reduces a size of the video stream, and a location of the cropped view within a full video frame of the video stream is remotely selectable from the desktop via the control interface, and
a codec adapted to selectively set a frame rate of the video stream prior to delivery of the video stream from the sensor to the desktop.

15. The system of claim 14, wherein the inspector is at least one of an optical inspection system, electron beam inspection system, electron beam review system, and optical review system.

16. The system of claim 14, wherein the substrate is one of a semiconductor wafer with integrated circuitry at least partially formed thereon and a mask for use in patterning integrated circuits on a semiconductor wafer.

17. The system of claim 14, wherein the decimator and the parser operate cooperatively to selectively down sample the video stream to a lesser degree when the video stream is selectively cropped to a higher degree, and to selectively down sample the video stream to a higher degree when the video stream is selectively cropped to a lesser degree.

18. The system of claim 14, further comprising an additional video source adapted to selectively produce an additional video stream for receipt by the desktop, under control of the user interface controls on the desktop.

19. A system for inspecting a substrate, the system comprising:
an inspector having a sensor that inspects the substrate and produces a video stream, and a control interface adapted to send and receive a control stream,
a network adapted to receive and transport the video stream and the control stream,
a desktop for receiving the video stream and the control stream over the network, the desktop having a display adapted to present the video stream, and the desktop having user interface controls adapted to control operation of the inspector by use of the control stream across the network,
a compressor adapted to selectively compress the video stream prior to delivery of the video stream from the sensor to the desktop, where the compressor compresses the video stream to a variable degree as specified through the user interface controls on the desktop,
a decimator adapted to selectively down sample the video stream prior to delivery of the video stream from the sensor to the desktop, where the decimator down samples the video stream to a variable degree as specified through the user interface controls on the desktop,
a parser adapted to selectively crop the video stream prior to delivery of the video stream from the sensor to the desktop, where the parser crops the video stream to a variable degree as specified through the user interface controls on the desktop, where the selective cropping reduces a size of the video stream, and
a frame grabber adapted to selectively set a frame rate of the video stream prior to delivery of the video stream from the sensor to the desktop, where the frame grabber sets the frame rate of the video stream to a variable degree as specified through the user interface controls on the desktop,
where the compressor, decimator, parser, and frame grabber all reside within the inspector.

* * * * *